United States Patent
Yang et al.

(10) Patent No.: US 8,870,763 B2
(45) Date of Patent: Oct. 28, 2014

(54) METHOD AND/OR SYSTEM FOR MULTICOMPARTMENT ANALYTE MONITORING

(75) Inventors: Ning Yang, Northridge, CA (US); Rebecca K. Gottlieb, Culver City, CA (US); Keith Nogueira, Northridge, CA (US); Xiaolong Li, Granada Hills, CA (US); Bradley Liang, Bloomfield Hills, MI (US); Brian T. Kannard, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 328 days.

(21) Appl. No.: 13/365,406

(22) Filed: Feb. 3, 2012

(65) Prior Publication Data
US 2013/0109942 A1      May 2, 2013

Related U.S. Application Data

(63) Continuation-in-part of application No. 13/282,096, filed on Oct. 26, 2011.

(60) Provisional application No. 61/551,844, filed on Oct. 26, 2011.

(51) Int. Cl.
| A61B 5/00 | (2006.01) |
| A61B 5/1495 | (2006.01) |
| A61B 5/145 | (2006.01) |
| A61B 5/1486 | (2006.01) |

(52) U.S. Cl.
CPC ........... *A61B 5/14532* (2013.01); *A61B 5/1495* (2013.01); *A61B 5/4839* (2013.01); *A61B 5/1451* (2013.01); *A61B 5/7242* (2013.01); *A61B 5/14865* (2013.01); *A61B 5/6849* (2013.01)
USPC ............................. 600/300; 600/347; 600/365

(58) Field of Classification Search
USPC ........................... 600/345, 347, 365; 604/504
See application file for complete search history.

(56) References Cited

U.S. PATENT DOCUMENTS

| 6,558,351 B1 | 5/2003 | Steil et al. |
| 2010/0162786 A1 | 7/2010 | Keenan |

OTHER PUBLICATIONS

PCT/US2012/028282: PCT: International search report and written opinion, mailed Jun. 19, 2012, 14 pages.
Kerstin, Rebrin et al: "Subcutaneous glucose predicts plasma glucose independent of insulin: implications for continuous monitoring", Am J Physiol Endocrinol Metab, Jan. 1, 1999, XP55029369, Retrieved from the Internet: URL:http://ajpendo.physiology.org/content/277/3/E561.short.
Ishan Barman, et al: "Accurate Spectroscopic Calibration for Noninvasive Glucose Monitoring by Modeling the Physiological Glucose Dynamics", Analytical Chemistry, vol. 82, No. 14, Jul. 15, 2010, pp. 6104-6114 XP55029372, ISSN:0003-2700, DOI:10.1021/ac100810e.
Erik Cheever: "Frequency Response and Active Filters", Aug. 17, 2009, XP55029363, Retrieved from the Internet: URL:http://www.swarthmore.edu/NatSci/echeeve1/Ref/FilterBkgrnd/Filters/html.
U.S. Appl. No. 13/282,096, filed Oct. 26, 2011, 50 pages.
U.S. Appl. No. 13/282,096, Notice to file missing parts, mailed Nov. 8, 2011, 6 pages.
U.S. Appl. No. 13/282,096, Response to notice to file missing parts, mailed Jan. 9, 2012, 19 pages.

*Primary Examiner* — Navin Natnithithadha
*Assistant Examiner* — Etsub Berhanu
(74) *Attorney, Agent, or Firm* — Berkeley Law & Technology Group, LLP

(57) ABSTRACT

Subject matter disclosed herein relates to monitoring and/or controlling levels of an analyte in bodily fluid. In particular, estimation of a concentration of the analyte in a first physiological compartment based upon observations of a concentration of the analyte in a second physiological compartment may account for a latency in transporting the analyte between the first and second physiological compartments.

15 Claims, 9 Drawing Sheets

METHOD AND/OR SYSTEM FOR MULTICOMPARTMENT ANALYTE MONITORING

This is a continuation-in-part of U.S. patent application Ser. No. 13/282,096, filed on Oct. 26, 2011 titled "Method and/or System for Multicompartment Analyte Monitoring," and claims the benefit of priority to U.S. Provisional Patent Appl. No. 61/551,844 titled "Method and/or System for Multicompartment Analyte Monitoring," filed on Oct. 26, 2011, assigned to the assignee of claimed subject matter, and incorporated herein by reference in its entirety.

BACKGROUND

1. Field

Subject matter disclosed herein relates to monitoring a concentration of an analyte in a physiological compartment.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals or trauma patients. As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

External infusion pumps are typically provided to control a rate of insulin infusion based, at least in part, on blood glucose measurements obtained from metered blood glucose samples (e.g., finger stick samples) or from processing signals received from a blood glucose sensor attached to a patient to provide sensor glucose measurements. By processing signals from such a blood glucose sensor, a patient's blood glucose level may be continuously monitored to reduce a frequency of obtaining metered blood glucose sample measurements from finger sticks and the like. However, measurements of blood glucose concentration obtained from processing signals from blood glucose sensors may not be as accurate or reliable as blood glucose sample measurements obtained from finger stick samples, for example. Also, parameters used for processing blood glucose sensors for obtaining blood glucose measurements may be calibrated from time to time using metered blood glucose sample measurements as reference measurements obtained from finger sticks and the like.

SUMMARY

Briefly, example embodiments may relate to methods, systems, apparatuses, and/or articles, for compensating for a latency in estimating a concentration of analyte in a physiological compartment. In a particular implementation, a method comprises: modeling a latency in transportation of an analyte between first and second physiological compartments; and compensating for the latency in estimating a concentration of the analyte in the first physiological compartment based, at least in part, on one or more measurements of a concentration of the analyte in the second physiological compartment. In one particular example, the analyte comprises glucose, the first physiological compartment comprises blood plasma, and the second physiological compartment comprises interstitial fluid. In another particular example, the one or more measurements are obtained based, at least in part, on one or more values of a sensor signal, and modeling the latency further comprises modeling the latency based, at least in part, on an estimated rate of change in the sensor signal. In another example, the estimated rate of change comprises an estimated first derivative of the sensor signal. In yet another example, the sensor signal value comprises a measured current responsive to a concentration of the analyte in the second physiological compartment. In yet another example implementation, estimating the concentration of the analyte in the first physiological compartment further comprises: multiplying the one or more sensor signal value by a first coefficient to provide a first product; multiplying the estimated rate of change by a second coefficient to provide a second product; and estimating the concentration of the analyte in the second physiological compartment based, at least in part, on a combination of said first and second products. In one example, the first and second coefficients may be determined based, at least in part, on an estimate of said latency. In another example, the first and second coefficients are selected based, at least in part, so as to provide a lowest error between measurements of said analyte in said second physiological compartment based on sensor measurements and reference samples of said analyte in said first physiological compartment. In yet another example, the coefficients are based, at least in part, on a substantially linear response of said sensor signal to said concentration of analyte in said second physiological compartment. In yet another example, the coefficients are based, at least in part, on a non-linear response of the sensor signal to the concentration of analyte in the second physiological compartment.

In another example implementation, the latency is based, at least in part, on a latency of a presence of glucose in a patient's interstitial fluid to affect a blood glucose concentration in said patient. For example, the latency may be defined based, at least in part, on a time for 63% of glucose in said interstitial fluid to be absorbed by the patient's blood.

In another example, implementation, modeling the latency comprises estimating a plurality of parameters of an estimator of the concentration of the analyte in the first physiological compartment, at least one of said parameters comprising an estimate of the latency. Compensating for the latency may comprise: applying the estimate of the latency to sensor signals generated responsive to the concentration of the analyte in the second physiological compartment to provide at least one latency compensated measurement; and computing an estimate of the concentration of the analyte in said first physiological compartment based, at least in part, on the at least one latency compensated measurement.

In another particular example implementation, a method comprises: concurrently computing multiple estimators of a concentration of an analyte in a first physiological compartment based, at least in part, on one or more measurements of a concentration of the analyte in a second physiological compartment; and selecting one of said estimators for determining a patient therapy based, at least in part, on a performance metric, wherein said selected estimator is based, at least in part on a modeled latency in transportation of said analyte between said first and second physiological compartments. In one particular example implementation, the performance metric comprises a mean absolute relative difference between reference samples of said concentration of said analyte in the first physiological compartment and estimates of the concentration of said analyte in the first physiological compartment are computed according to said selected estimator. In another particular example implementation, the selected estimator is based, at least in part, on a plurality of estimated parameters including an estimate of a latency in transportation of said analyte between said first and second physiological compartments.

In another example, implementation, an apparatus comprises: a sensor to generate a signal responsive to a concentration of an analyte in a second physiological compartment; and a processor to: model a latency in transportation of the analyte between the second physiological compartment and a first physiological compartment; and compensate for the latency in estimating a concentration of the analyte in the first physiological compartment based, at least in part, on the signal responsive to the concentration of the analyte in the second physiological compartment. In another implementation, the one or more measurements are obtained based, at least in part, on one or more values of a sensor signal, and wherein said process is further to model the latency based, at least in part, on an estimated rate of change in the sensor signal. For example, the estimated rate of change comprises an estimated first derivative of the sensor signal. Also, the sensor signal value may comprise a measured current responsive to a concentration of said analyte in said second physiological compartment.

In another example implementation, an apparatus comprises: means for modeling a latency in transportation of an analyte between first and second physiological compartments; and means for compensating for the latency in estimating a concentration of the analyte in the first physiological compartment based, at least in part, on one or more measurements of a concentration of the analyte in the second physiological compartment.

In another implementation, an article comprises: a non-transitory storage medium having machine-readable instructions stored thereon which are executable by a special purpose computing apparatus to: model a latency in transportation of an analyte between first and second physiological compartments; and compensate for the latency in estimating a concentration of the analyte in the first physiological compartment based, at least in part, on one or more measurements of a concentration of the analyte in the second physiological compartment. The one or more measurements may be obtained based, at least in part, on one or more values of a sensor signal, and wherein said process is further to model the latency based, at least in part, on an estimated rate of change in said sensor signal. The estimated rate of change may comprise an estimated first derivative of the sensor signal. Also, the sensor signal value comprises a measured current responsive to a concentration of said analyte in said second physiological compartment.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described method(s) according to one or more particular implementations based upon one or more signals generated by the sensor.

Briefly, other example embodiments may relate to methods, systems, apparatuses, and/or articles, for compensating for a latency in estimating a concentration of analyte in a physiological compartment. In a particular implementation, a method comprises modeling a latency in transportation of an analyte between first and second physiological compartments; and compensating for the latency in estimating a concentration of the analyte in the first physiological compartment based, at least in part, on one or more measurements of a concentration of the analyte in the second physiological compartment by: (1) integrating a difference between a sensor signal value and an offset value to provide an integrated expression; and (2) determining the estimated concentration based, at least in part, on a computed rate of change in the integrated expression. In one example implementation, the method may further comprise applying a weight to the integrated expression according to the modeled latency. In another example implementation, determining the estimated concentration may further comprise combining the integrated expression with a term based, at least in part, on the modeled latency to provide a combined expression; and determining the estimated concentration based, at least in part, on a computed rate of change in the combined expression. In another example implementation, the analyte comprises glucose, the first physiological compartment comprises blood plasma, and the second physiological compartment comprises interstitial fluid. In another implementation, the sensor signal value comprises a measured current responsive to the concentration of the analyte in the second physiological compartment.

In another implementation, the latency is based, at least in part, on a latency of a presence of glucose in a patient's interstitial fluid to affect a blood glucose concentration in the patient. In one example implementation, the latency is defined based, at least in part, on a time for 63% of glucose in the interstitial fluid to be absorbed by the patient's blood.

In another implementation, an apparatus comprises: a sensor to generate a signal responsive to a concentration of an analyte in a second physiological compartment; and a processor to: model a latency in transportation of the analyte between the second physiological compartment and a first physiological compartment; and compensate for the latency in estimating a concentration of the analyte in the first physiological compartment based, at least in part, on the signal responsive to the concentration of the analyte in the second physiological compartment by: (1) integrating a difference between a sensor signal value and an offset value to provide an integrated expression; and (2) determining the estimated concentration based, at least in part, on a computed rate of change in the integrated expression. In one particular implementation, the sensor signal value may comprise a measured current responsive to a concentration of the analyte in the second physiological compartment. In another particular implementation, the analyte comprises glucose, the first physiological compartment comprises blood plasma, and the second physiological compartment comprises interstitial fluid. In another implementation, the sensor signal value comprises a measured current responsive to the concentration of the analyte in the second physiological compartment. In another implementation, the latency is based, at least in part, on a latency of a presence of glucose in a patient's interstitial fluid to affect a blood glucose concentration in the patient. In another implementation, the latency is defined based, at least in part, on a time for 63% of glucose in said interstitial fluid to be absorbed by the patient's blood. In yet another implementation, the processor may further generate a command to one or more infusion pumps computed based, at least in part, on the estimated concentration.

In another embodiment, an article comprises: a non-transitory storage medium having machine-readable instructions stored thereon which are executable by a special purpose computing apparatus to: model a latency in transportation of an analyte between first and second physiological compartments; and compensate for the latency in estimating a concentration of the analyte in the first physiological compartment based, at least in part, on one or more measurements of a concentration of the analyte in the second physiological compartment by: (1) integrating a difference between a sensor signal value and an offset value to provide an integrated expression; and (2) determining said estimated concentration based, at least in part, on a computed rate of change in the integrated expression. In a particular implementation, the instructions are further executable by the special purpose computing apparatus to determine said estimated concentration by: combining said integral expression with a term based, at least in part, on the modeled latency to provide a combined expression; and determining the estimated concentration based, at least in part, on a computed rate of change in the combined expression. In another particular implementation, the analyte comprises glucose, the first physiological compartment comprises blood plasma, and the second physiological compartment comprises interstitial fluid. In yet another implementation, the sensor signal value comprises a measured current responsive to the concentration of the analyte in the second physiological compartment.

In another embodiment, an apparatus comprises: means for modeling a latency in transportation of an analyte between first and second physiological compartments; and means for compensating for the latency in estimating a concentration of the analyte in the first physiological compartment based, at least in part, on one or more measurements of a concentration of the analyte in the second physiological compartment by: (1) integrating a difference between a sensor signal value and an offset value to provide an integrated expression; and (2) determining said estimated concentration based, at least in part, on a computed rate of change in the integrated expression.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described methods) according to one or more particular implementations based upon one or more signals generated by the sensor.

BRIEF DESCRIPTION OF THE FIGURES

Non-limiting and non-exhaustive features will be described with reference to the following figures, wherein like reference numerals refer to like parts throughout the various figures.

DETAILED DESCRIPTION

Figure 1:
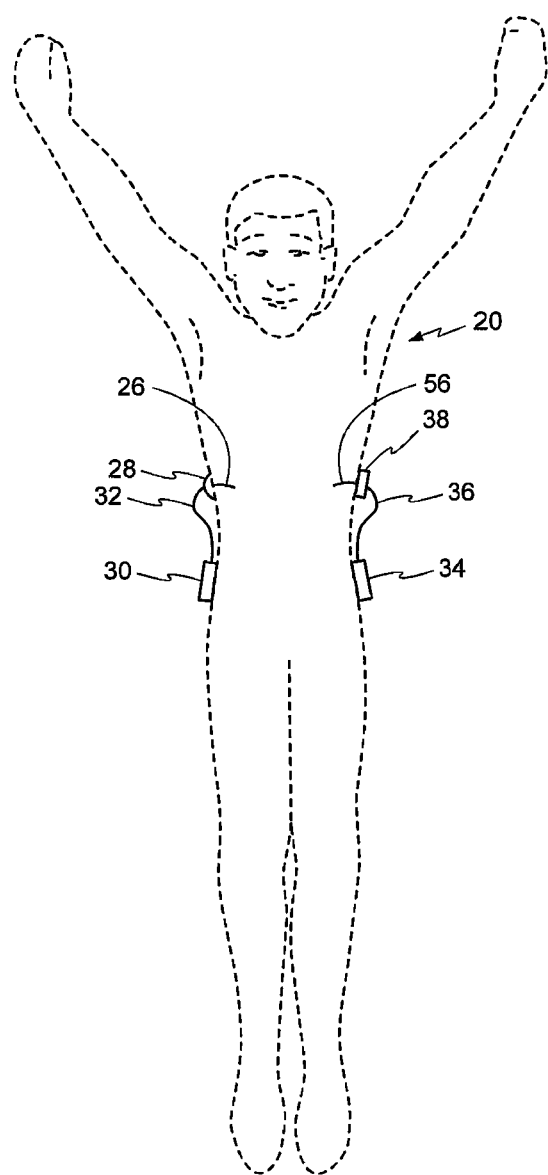
FIG. 1 is a front view of example devices located on a body in accordance with an embodiment.
Figure 2:
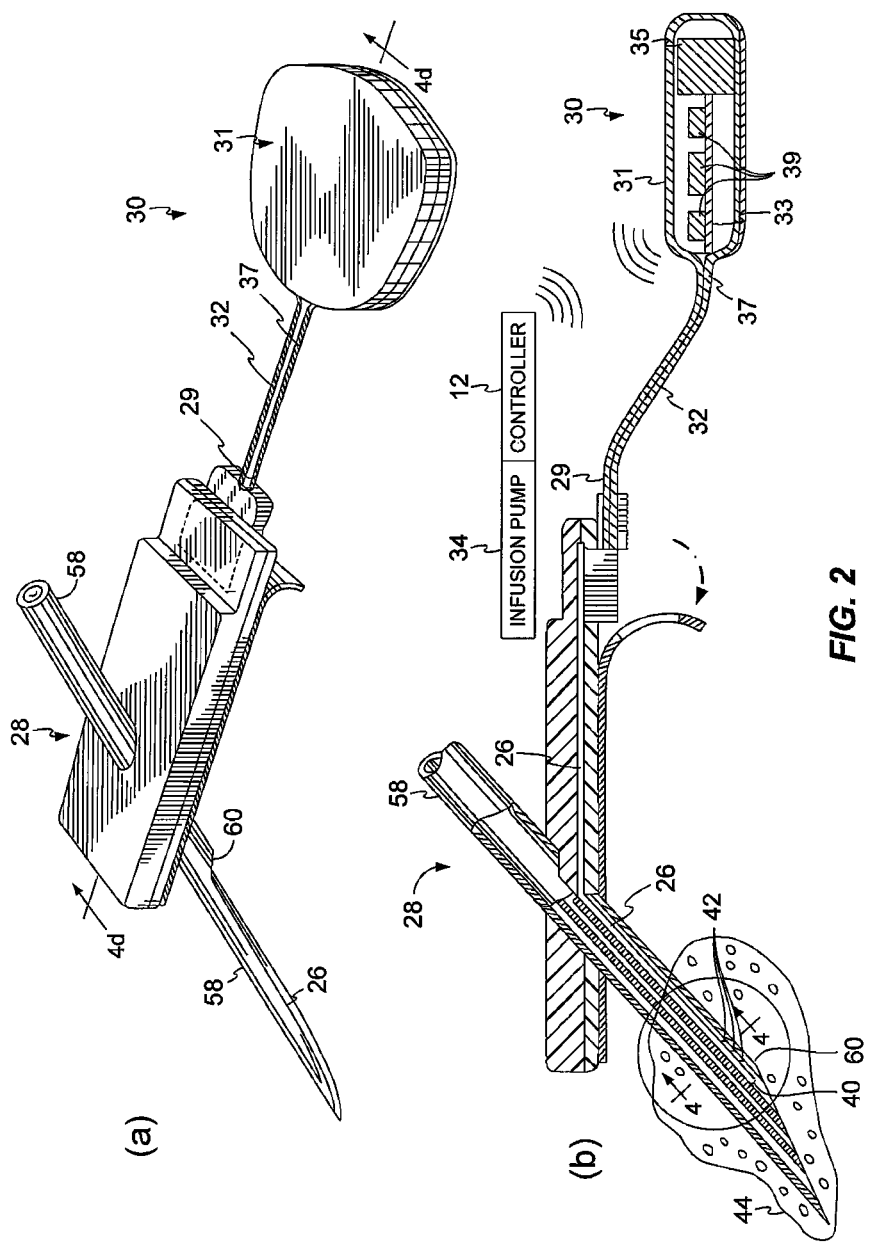
FIG. 2(a) is a perspective view of an example glucose sensor system for use in accordance with an embodiment.
FIG. 2(b) is a side cross-sectional view of a glucose sensor system of FIG. 2(a) for an embodiment.
FIG. 2(c) is a perspective view of an example sensor set of a glucose sensor system of FIG. 2(a) for an embodiment.
FIG. 2(d) is a side cross-sectional view of a sensor set of FIG. 2(c) for an embodiment.
Figure 2:
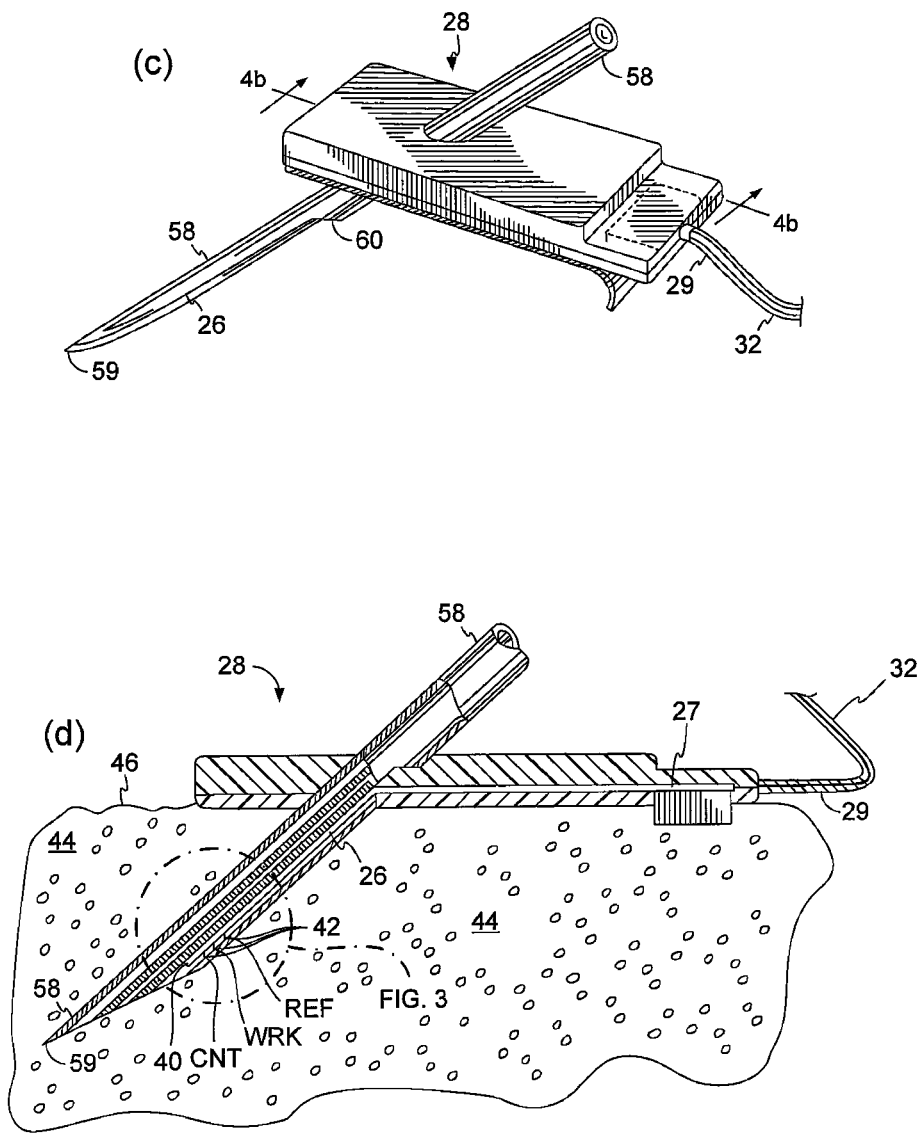

In an example glucose control system environment, blood-glucose measurements may be obtained from a blood glucose sensor in any one of several different specific applications such as, for example, aiding in the application of insulin therapies in a hospital environment, controlling infusion of insulin in a patient-operated insulin infusion systems, just to name a few examples. In particular applications, a blood glucose sensor may be employed as part of a system to control infusion of insulin so as to control/maintain a patient's blood glucose within a target range, thus reducing a risk that the patient's blood glucose level transitions to dangerous extreme levels in the absence of action from the patient or treating attendant.

According to certain embodiments, example systems as described herein may be implemented in a hospital environment to monitor or control levels of glucose in a patient. Here, as part of a hospital or other medical facility procedure, a caretaker or attendant may be tasked with interacting with a patient's glycemic management system to, for example: enter blood-glucose reference measurements into control equipment to calibrate blood glucose measurements obtained from glucose sensors, make manual adjustments to devices, and/or make changes to therapies, just to name a few examples. Alternatively, a patient or other non-medical professional may be responsible for interacting with a closed-loop system to, for example, provide updated measurements of blood-glucose concentration obtained from blood glucose reference samples or the like.

In a typical continuous glucose monitoring environment, a glucose sensor may be inserted into a patient's subcutaneous tissue to observe a concentration or level of glucose present in the interstitial fluid. Based, at least in part, on a concentration of level of glucose observed to be present in interstitial fluid, a level or concentration of glucose present in blood plasma may be estimated or measured. Glucose entering the blood by, for example, digestion of a meal, etc., may not substantially affect a glucose level or concentration in interstitial fluid until after a physiological delay or latency. If a blood glucose level in a patient is rapidly rising or falling, estimates of blood glucose level or concentration based upon a blood glucose level or concentration observed in interstitial fluid from a glucose sensor may be inaccurate.

According to an embodiment, a delay or latency in transportation of an analyte between first and second physiological compartments may be modeled. In alternative implementations, a metabolic decay in an analyte in connection with transportation between physiological compartments may also be modeled. A process for estimating a concentration of the analyte in the first physiological compartment based, at least in part, on measurements of a concentration of the analyte in a second physiological compartment may compensate for the modeled delay. Similarly, a process for estimating a concentration may also compensate for a modeled metabolic decay in an analyte.

In a particular implementation in a continuous glucose monitoring system, a delay or latency in the transportation of glucose from blood to interstitial fluid may be modeled. A process for estimating a concentration of blood glucose based, at least in part, on an observed concentration of glucose in interstitial fluid may then compensate for this delay. Likewise, a process for estimating a concentration of glucose in blood from an observed concentration of glucose in interstitial fluid may also compensate for a metabolic decay of glucose. Here, compensating for this delay or decay may reduce inaccuracies in estimating blood glucose which is rapidly rising or falling. It should be understood, however, that this is merely an example implementation presented for the purpose of illustration, and that claimed subject matter is not limited in this respect. For example, other implementations may be directed to estimating a concentration of analytes in a physiological compartment other than glucose such as, for example, low-density lipoprotein, amino acids, just to provide a couple of examples. Also, other implementations may be directed to modeling a delay or latency in transportation of an analyte between physiological compartments, and/or metabolic decay of an analyte in physiological compartments, other than blood stream and interstitial fluid. For example, other embodiments may be directed to modeling a delay, latency or decay in connection with gastric transport or nasal transport.

Figure 3:
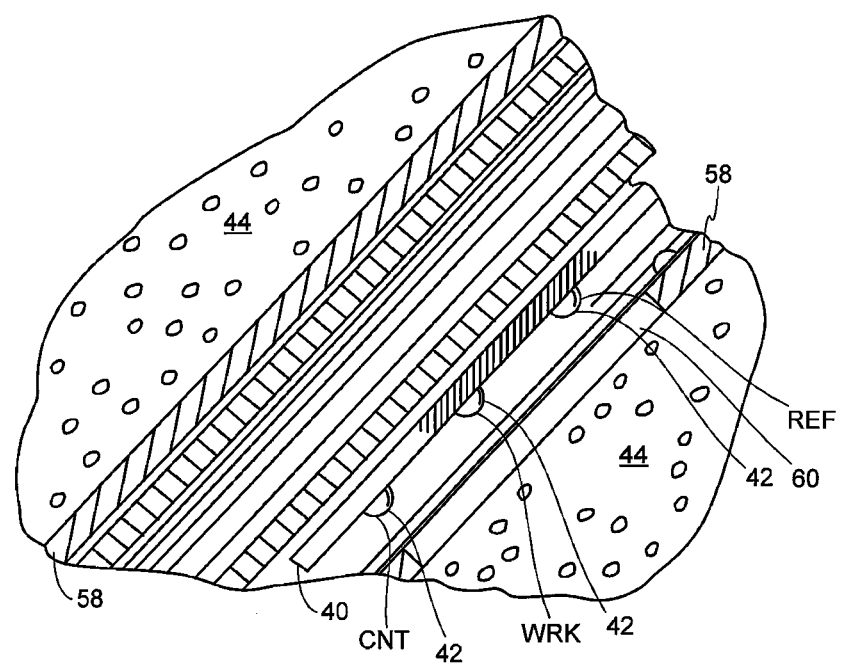
FIG. 3 is a cross sectional view of an example sensing end of a sensor set of FIG. 2(d) for an embodiment.
Figure 4:
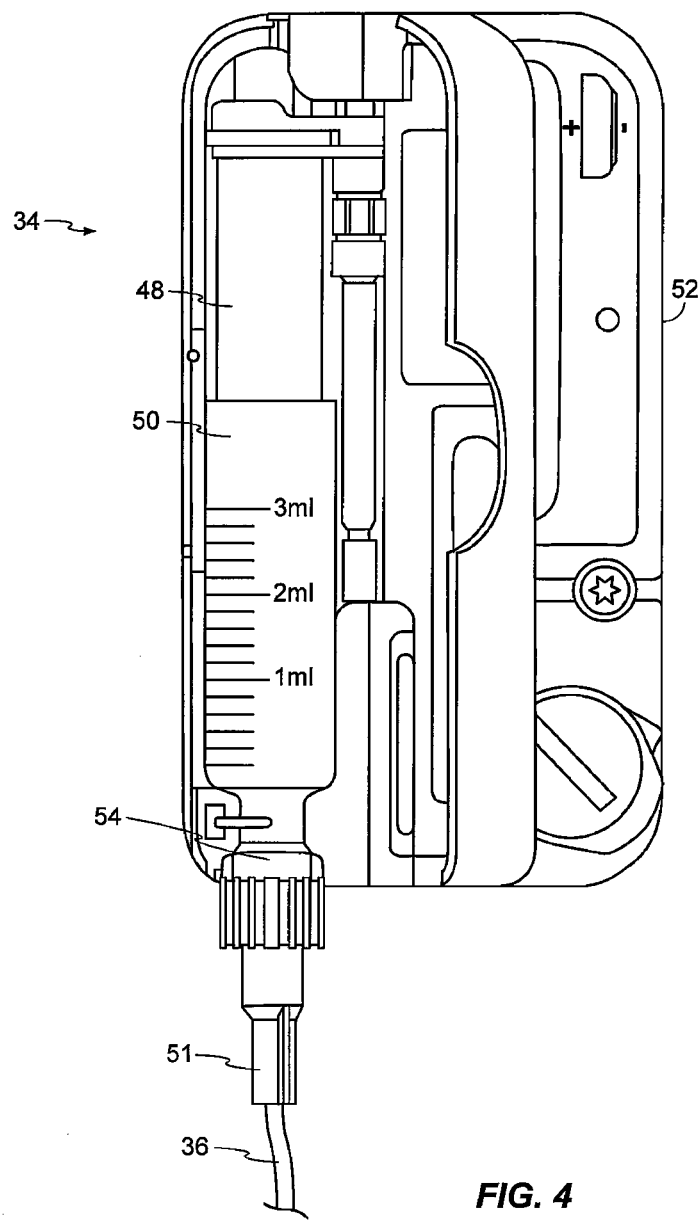
FIG. 4 is a top view of an example infusion device with a reservoir door in an open position, for use according to an embodiment.
Figure 5:
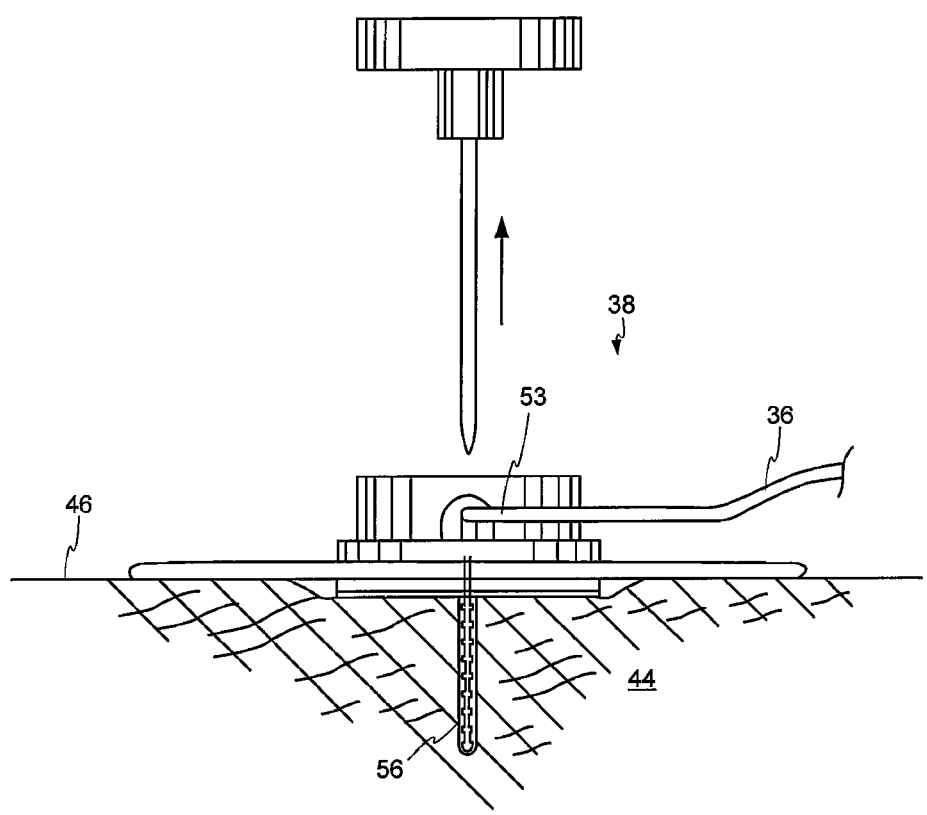
FIG. 5 is a side view of an example infusion set with an insertion needle pulled out, for use according to an embodiment.

FIGS. 1 through 5 illustrate example glucose control systems in accordance with certain embodiments. Such glucose control systems may be used, for example, in controlling a patients glucose level about a target range as discussed above. It should be understood, however, that these are merely examples of particular systems that may be use for controlling a patient's glucose level about a target range and that claimed subject matter is not limited in this respect. FIG. 1 is a front view of example devices located on a body in accordance with certain embodiments. FIGS. 2(a)-2(d) and 3 show different views and portions of an example glucose sensor system for use in accordance with certain embodiments enabling continuous monitoring of a patient's blood glucose level. FIG. 4 is a top view of an example optional infusion device with a reservoir door in an open position in accordance with certain embodiments. FIG. 5 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 1. As shown in FIGS. 2a and 2b, telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 2d and 3. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 2(c) and 2(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample a sensor signal current (ISIG, not shown) and store the sampled digital sensor values (DSIG) in a memory. Digital sensor values DSIG may be periodically transmitted from a memory to a controller 12, which may be included in an infusion device.

With reference to FIGS. 1 and 4, a controller 12 may process digital sensor values DSIG and generate commands for infusion device 34. Infusion device 34 may respond to commands and actuate a plunger 48 that forces insulin out of a reservoir 50 that is located inside an infusion device 34. In an alternative implementation, glucose may also be infused from a reservoir responsive to commands using a similar and/or analogous device (not shown). In alternative implementations, glucose may be administered to a patient orally.

Also, controller 12 may collect and maintain a log or history of continuous measurements of a patient's blood glucose level to, for example, allow for characterization of a patient's glycemic trends. For example, and as illustrated below in particular example embodiments, a history of continuous blood glucose sensor measurements may enable prediction of a patient's blood glucose level at some time in the future.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 1 and 5). With reference to FIG. 5, insulin may be forced through infusion tube 36 into infusion set 38 and into a body of a patient. Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 4) and subcutaneous tissue 44 of a user's body 16.

As pointed out above, particular implementations may employ a closed-loop system as part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Figure 6:
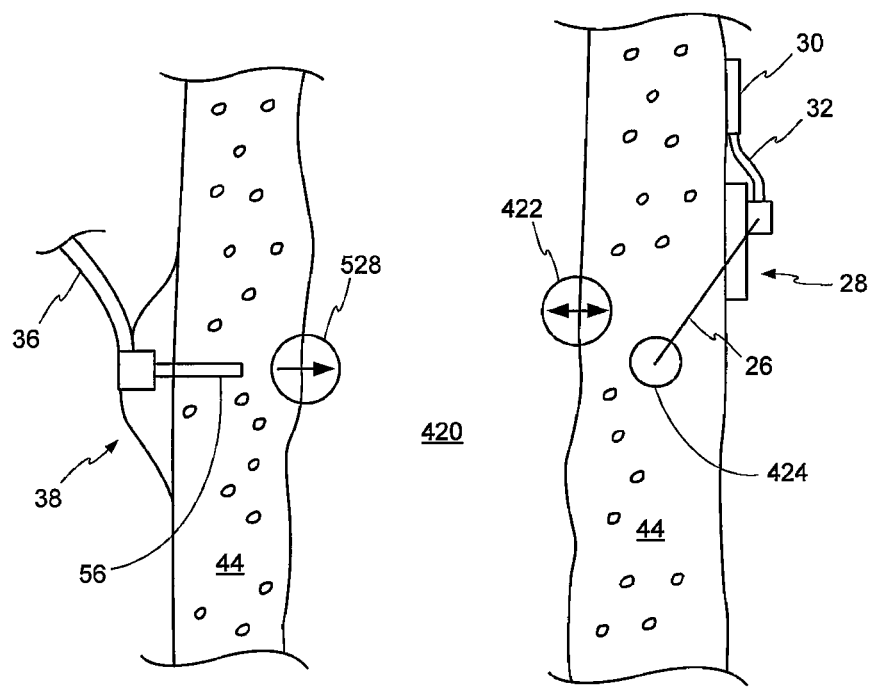
FIG. 6 is a cross-sectional view of an example sensor set and an example infusion set attached to a body in accordance with an embodiment.

FIG. 6 is a cross-sectional view of an example sensor set and an example infusion set that is attached to a body in accordance with an embodiment. In particular example implementations, as shown in FIG. 6, a physiological delay or latency may arise from a time that transpires while glucose transitions between blood plasma 420 and interstitial fluid (ISF). This example delay may be represented by a circled double-headed arrow 422. As discussed above with reference to FIG. 1-3, a sensor may be inserted into subcutaneous tissue 44 of body 20 such that electrode(s) 42 (e.g., of FIGS. 3 and 4) near a tip of sensor 40 are in contact with ISF. However, a parameter to be estimated may include a concentration of glucose in blood plasma.

Glucose may be carried throughout a body in blood plasma 420. Through a process of diffusion, glucose may move from blood plasma 420 into ISF of subcutaneous tissue 44 and vice versa. As blood glucose level changes, so may a glucose level of ISF. However, a glucose level of ISF may lag behind blood glucose level 18 due, at least in part, on a duration for a body to achieve glucose concentration equilibrium between blood plasma 420 and ISF. Some studies have shown that glucose lag times between blood plasma and ISF may vary between, e.g., 0.0 to 30.0 minutes. Some parameters that may affect such a glucose lag time between blood plasma and ISF are an individual's metabolism, a current blood glucose level, whether a glucose level is rising or falling, combinations thereof, and so forth, just to name a few examples.

A chemical reaction delay 424 may be introduced by sensor response times, as represented by a circle 424 that surrounds a tip of sensor 26 in FIG. 6. Sensor electrodes may be coated with protective membranes that keep electrodes wetted with ISF, attenuate the glucose concentration, and reduce glucose concentration fluctuations on an electrode surface. As glucose levels change, such protective membranes may slow the rate of glucose exchange between ISF and an electrode surface. In addition, there may be chemical reaction delay(s) due to a reaction time for glucose to react with glucose oxidase GOX to generate hydrogen peroxide and a reaction time for a secondary reaction, such as a reduction of hydrogen peroxide to water, oxygen, and free electrons.

Figure 7:
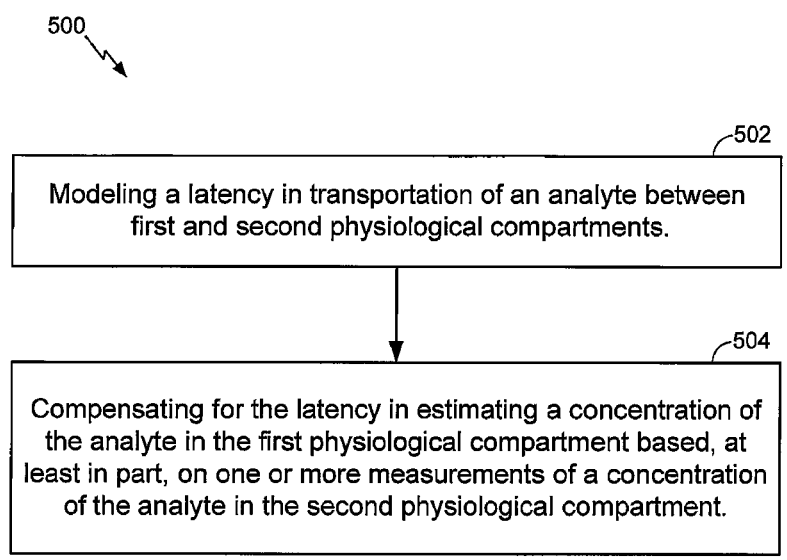
FIG. 7 is a flow diagram of a process for compensating for a latency in estimating a concentration of an analyte in a physiological compartment, according to an embodiment.

Previous techniques for estimating a concentration blood glucose based on sensor signals have entailed modeling a concentration of glucose present in blood based on contemporaneous sensor measurements of a concentration of glucose present in ISF. As pointed out above, this particular technique may lead to inaccurate estimates of the concentration of glucose present in blood in conditions where blood glucose is rapidly rising. FIG. 7 is a flow diagram of a process 500 for compensating for a latency in estimating a concentration of an analyte in a physiological compartment. In particular implementations described below, a latency in the transportation an analyte (glucose in particular examples below) between physiological compartments (ISF and blood plasma in particular examples below) is modeled at block 502. A process of estimating a concentration of the analyte present in one of the physiological compartments based upon an observed concentration of the analyte in the other physiological compartment may then compensate for this modeled latency at block 504. In a particular implementation, a relationship between a concentration of glucose in blood (8) and a concentration of glucose in ISF (I) may be expressed as follows:

$$V \frac{dI}{dt} = k_M A(B - I) - K_U V I \tag{1}$$

where:
I is the concentration of glucose in ISF;
B is the concentration of glucose in blood;
V is the ISF volume;
A is the effective mass transfer surface area;
$k_M$ is a glucose mass transfer coefficient; and
$k_U$ is a rate of glucose uptake by neighboring cells.
An expression for B may then be provided as follows:

$$B = \left(1 + \frac{k_U V}{k_M A}\right) I + \frac{V}{k_M A} \frac{dI}{dt}. \tag{2}$$

As pointed out above, glucose monitor 30 may measure a continuous electrical current signal value (ISIG) generated by glucose sensor 26 in response to a concentration of glucose present in ISF of the user's body. In one particular example, glucose monitor 30 may sample the ISIG from glucose sensor 26 at a sampling rate of once every 10.0 seconds (e.g., stored as DSIG as discussed above). Accordingly, in specific implementations, I may be observed directly based, at least in part, on ISIG. In certain particular applications, and as described in U.S. patent application Ser. No. 12/345,477, filed Dec. 29, 2008, and Ser. No. 13/239,265, filed on Sep. 21, 2011, both assigned to the assignee of claimed subject matter, a value of ISIG may be observed to respond as a linear function of I. As such, I(t) may be observed to be a substantially linear function of ISIG as shown in expression (3) follows:

$$I(t) = s \times ISIG(t) + c, \tag{3}$$

Where s and c are sensor-dependent parameters.
Combining expressions (2) and (3) may then provide an estimator of B as follows:

$$B = s \times [\alpha \times ISIG'(t) + \beta \times ISIG(t)] + \beta \times c \tag{4}$$

Where:

$$\alpha = \frac{V}{k_M A} \text{ and } \beta = 1 + \alpha k_U.$$

In one particular implementation, values for $\alpha$ and $\beta$ may be set as constants. Assuming that there is a small glucose level in ISF, $\beta$ may approach one. In at least one clinical study, an average error appeared to be lowest if a is about 5.5 minutes. If sensor signal bias is to be ignored or assumed to be negligible, the term $\beta \times c$ in expression (4) approaches zero, and a single blood glucose reference sample may be used to solve for s to complete the estimator shown in expression (4) by setting B to the obtained blood glucose reference sample.

It has been observed, however, that values for $\alpha$ and $\beta$ may be patient-specific and time-dependent. As such, values for $\alpha$ and $\beta$ may be estimated by obtaining multiple blood glucose reference samples. Again setting the term $\beta \times c$ in expression (4) to zero, equating the estimator of expression (4) to two blood glucose reference samples separated in time (e.g., separated by one hour or less) values for s×α and s×β in the estimator for expression (4) may then be determined using least square error or other "best fit" parameter estimation techniques. In particular example embodiments, a parameter estimation technique may constrain a value for β to be 0.5 to 10.0 mg/dl/nA while a ratio of α/β may be constrained to be in a range of 2.0 to 10.0 minutes. In one particular implementation, a ratio of α/β may represent a time delay as the time at which a concentration in ISF reaches 63%. Here, values of α and β may be searched within ranges which give a lowest error at multiple calibration points pairing sensor blood glucose with blood glucose reference samples. If sensor signal bias is not negligible or not insignificant, parameters for the estimator of expression (4) may be determined by setting B to three consecutive blood glucose reference samples (e.g., less than one hour apart). As indicated above, values for s×α, s×β and β×c providing a "best fit" or smallest error may be selected. Here, values for α and β may be constrained within ranges. In one particular implementation of a sensor, values for c may be similarly constrained to be between −3.0 seconds and 3.0 seconds. In the particular example above, expression (3) models I(t) as a linear function of ISIG (t). In other implementations, I(t) may be observed to be a non-linear function of ISIG (t) as discussed above in the aforementioned U.S. patent application Ser. No. 13/239,265. In one particular implementation, such a non-linear function of ISIG (t) may be expressed as an exponential function in expression (5) follows:

$$I(t) = (ISIG(t) + b)^a + d, \quad (5)$$

Where: a, b and d are sensor and physiological dependent parameters.

According to an embodiment, b may reflect a sensor's non-linear response to the presence of glucose in ISF while d may reflect a patient's particular physiology. Expressions (2) and (5) may be combined to provide an estimator of B at expression (6) as follows:

$$\frac{dI(t)}{dt} = a \times ISIG'(t) \times (ISIG(t) + b)^{a-1} \quad (6)$$

$$B = \beta \times [(ISIG(t) + b)^a + d] + \alpha[a \times ISIG'(t) \times (ISIG(t) + b)^{a-1}]$$

As discussed above in connection with determining parameters for the estimator of expression (4), parameters of the estimator for B shown of expression (6) (e.g., α, β, a, b and d) may be obtained based on a series of blood glucose reference samples. As pointed out above, by equating multiple blood glucose reference samples to B in expression (6), parameters of interest may be solved to provide a "best fit" for the estimator. In determining a best fit for parameters in expression (6), initial ranges may be set for a (e.g., 1.2 to 1.8), b (−5 to 20), α (e.g., 0 to 3) and β (e.g., 0.8 to 2.0). It should be understood, however, that these are merely example ranges provided for illustration, and that claimed subject matter is not limited in these respects.

In particular implementations, values for ISIG'(T) as implemented in the estimators of expressions (4) and (6) at time T may be determined based, at least in part, on values for ISIG(t) obtained over a time period. Techniques for determining ISIG'(T) provided herein are merely example techniques, and it should be understood that any of these techniques mentioned, or techniques not mentioned, may be used without deviating from claimed subject matter. Applying a finite difference technique, a value for may be determined as follows:

$$ISIG'(T) = [ISIG(T) - ISIG(T-k)]/(T-k),$$

where k is selected to filter noisy samples of ISIG.

Applying a Savitzky-Golay filter, as discussed in Savitzky, A; Golay, M J E: Smoothing and differentiation of data by simplified least squares procedures, *Analytical Chemistry* 1964; 36 (8): 1627-1639, by performing a local polynomial regression of degree M on a series of values (e.g., of at least M+1 values equally spaced), ISIG'(t) at discrete points may be computed as follows:

$$g_i = \sum_{n=i-N}^{i} c_n^M ISIG_{i+n} \quad (7)$$

$$ISIG'_i = \frac{g_i}{\Delta}, \quad (8)$$

where:
N>M and values for c represent sample Savitzky-Golay coefficients.

In another particular implementation, Fourier decomposition may be used to compute a first derivative in the frequency domain as discussed in Jauberteau, F; Jauberteau, J L: Numerical differentiation with noisy signal, *Applied Mathematics and Computation* 2009; 215: 2283-2297. A piecewise cubic spline interpolation may be used smooth values for ISIG(t). Its Fourier coefficients may give an approximation of ISIG'(t).

The particular example implementations outlined above estimate a blood glucose concentration based, at least in part, on an estimated rate of change for ISIG (t) (e.g., ISIG' (t) computed using any of the techniques identified above or other techniques). In certain application, computation of ISIG' (t) over a short period of time the presence of noise may distort an actual rate of change of a glucose concentration in ISF. In an alternative implementation, B may be estimated or modeled based, at least in part, on an estimated delay for a presence of glucose in blood to be detected in ISF. Expression (9) may model the behavior of ISIG (t) as a linear function of B (t) as follows:

$$ISIG(t) = mB(t-\tau) + k, \quad (9)$$

where:
m is a slope indicative of a responsiveness of ISIG (t) to the presence of blood glucose;
τ is a delay for a presence of glucose in blood to be detected in ISF; and
k is an offset constant.

From expression (9), an estimator of B may be provided in expression (10) as follows:

$$B(t) = [ISIG(t+\tau) - k]/m \quad (10)$$

By estimating τ, k, and m, an estimate of B(t) may be provided as a function of ISIG (t). By obtaining a series of blood glucose reference measurements paired with sampled values of ISIG (t) over a time period, values for τ, k, and m may be estimated using any one of several different "best fit" parameter estimation techniques such as, for example, the so-called Taguchi method as shown in Intelligent Fault Diagnosis, Prognosis and Self-Reconfiguration for nonlinear Dynamic Systems Using Soft Computing Techniques, IEEE Conference, 2006, Paul, P. Lin, Xiaolong Li. However, other multi-parameter estimation techniques may be used. In one particular implementation, values for τ, k, and m may each be constrained to be in a particular range. In a particular example implementation, τ may range from 1.0 to 10.0 minutes, k may range from −50.0 to 10.0 nA and m may range from 3.0 to 8.0 nA/mg/dl. It should be understood, however that these are merely ranges that may be applied with a particular sensor in a particular implementation, and that claimed subject matter is not limited in this respect.

A value for τ may represent or be affected by a delay for the presence of glucose in blood plasma to be detected in ISF. As such, values for τ may change over time or as conditions change (e.g., an environment of rising blood glucose concentration or falling blood glucose concentration). Likewise, values for m and k may be affected by specific characteristics of a blood glucose sensor which may change over time with normal use. Accordingly, in a particular implementation, estimates for values for τ, k, and m may be updated from time to time or on receipt of a blood glucose reference sample at a controller.

As pointed out above, a glucose sensor may behave differently over time through normal use and wear. Also, a newly implanted glucose sensor may not have provided an opportunity to obtain a lengthy history of behavior or pairings of blood glucose reference samples with sampled values of ISIG(t) sufficient for accurate or useful estimates of τ, k, or m for estimating B (t) from expression (10). Accordingly, in a particular implementation, a different technique may be used initially for estimating blood glucose such as, for example, techniques that do not rely on an estimated delay for a presence of glucose in blood to be detected in ISF. Such techniques may model a blood glucose concentration as a function of ISIG as shown in expression (11) as follows:

$$SBG=SR*ISIG+offset, \quad (11)$$

Where:
SR is a sensitivity ratio computed from correlated pairings of ISIG and blood glucose reference samples over time;
SBG is the estimated sensor blood glucose; and
offset is an offset computed from correlated pairings of ISIG and blood glucose reference samples over time.

In particular example implementations, techniques for obtaining an estimated blood glucose SBG according to expression (11) may be found in U.S. patent application Ser. No. 12/345,477, filed Dec. 29, 2008, and U.S. patent application Ser. No. 13/239,265, filed on Sep. 21, 2011, both assigned to the assignee of claimed subject and incorporated herein by reference. It should be understood, however, that these are merely example techniques for computing an estimate of B without estimating a delay for a presence of glucose in blood to be detected in ISF, and that claimed subject matter is not limited in these respects.

In one implementation, multiple techniques may be applied concurrently until a reliable estimate of a delay for a presence of glucose in blood to be detected in ISF emerges. For example, as a new glucose sensor is implanted in a patient, techniques according to expressions (10) and (11) may be used to estimate B as a function of ISIG for a period of time (e.g., six to twelve hours). If the measured performance of the technique according to expression (10) surpasses the technique according to expression (11), according to a particular performance metric, the technique of expression (10) may be selected to provide an estimate of B for display, recommendation of an appropriate insulin therapy, controlling an insulin pump, just to name a few examples. Such a performance metric may comprise, for example, a mean absolute relative difference (MARD) computed according to expression (12) as follows:

$$MARD=100 \times (MBG-SBG)/MGB, \quad (12)$$

where:
MBG is a blood glucose concentration value obtained from a blood glucose reference sample; and
SBG is a sensor blood glucose concentration measurement based upon application of an ISIG value to either a technique according to expression (10) or a technique according to expression (11).

In an alternative embodiment, combining expressions (2) and (3) may provide an alternative estimator of B as follows:

$$B = \gamma \frac{dISIG(t)}{dt} + \chi(ISIG(t) - \text{offset}) \quad (13)$$

Where:

$$\gamma = s\frac{V}{k_M A} \text{ and } \chi = s\left(1 + \frac{k_U V}{K_M A}\alpha k_U\right).$$

In one particular implementation, the ratio γ/χ may represent a modeled delay or latency for 63% of glucose in ISF to be absorbed in blood glucose in a step response. Expression (13) may then be simplified as expression (14) follows:

$$B = \chi\left(\text{delay}\frac{dISIG(t)}{dt} + (ISIG(t) - \text{offset})\right) \quad (14)$$

Where:

$$\text{delay} = \frac{\gamma}{\chi}.$$

The term $$\frac{dISIG(t)}{dt}$$

in expression (14) may be difficult to reliably measure or compute by typical techniques for computing a derivative of a noisy signal such as ISIG(t). However, an integration of both left-hand and right-hand sides of expression over time may avoid the complexities and unreliability of computing a rate of change of a noisy signal as follows as shown in expression (15) as follows:

$$\int B dt = \int \chi \times \text{delay} \times \frac{dISIG(t)}{dt} dt + \int \chi \times \quad (15)$$
$$(ISIG(t) - \text{offset})dt$$
$$= \chi \times \text{delay} \int \frac{dISIG(t)}{dt} dt + \int \chi \times$$
$$(ISIG(t) - \text{offset})dt$$

The term $$\int \frac{dISIG(t)}{dt} dt$$

in expression (15) may be approximated by a value ΔISIG(t) representing a difference between a present sensor signal value ISIG(t) and an initial ISIG(t₀) to simplify expression (15) as expression (16) as follows:

$$\int B dt = \chi \times \text{delay} \times \Delta ISIG(t) + \int \chi \times (ISIG(t) - \text{offset})dt. \quad (16)$$

A sensor blood glucose measurement (SG(t)) may then be obtained by determining a rate of change of the right-hand portion of expression (16) as shown in expression (17) as follows:

$$SG(t) = \frac{d\left(\chi \times \text{delay} \times \Delta ISIG(t) + \int \chi \times (ISIG(t) - \text{offset}) dt\right)}{dt} \quad (17)$$

By integrating the expression $\chi \times (ISIG(t) - \text{offset})$, unbiased noise in the signal for ISIG(t) over an integration interval may be substantially cancelled and/or removed. Here, such an integration interval may commence after a sensor has achieved a desired stability (e.g., 30 to 60 minutes following stabilization) and continue for the life of the sensor. In particular embodiments, an integrated expression such as $\int \chi \times (ISIG(t) - \text{offset}) dt$ in expression (17) may be computed using any one of several numerical integration computation techniques to provide a numerical value to approximate the value of the expression. Accordingly, the right-hand portion of expression (17) may be reliably computed using well known techniques for computing a derivative and/or rate of change of a signal or function. Values for $\chi$, delay and offset for use in computing SG(t) according to expression (17) the may be computed using a calibration process that attempts to reduce or minimize an expected error in SG(t) in comparison with blood glucose reference sample values BG. In particular implementations, a value for offset may be treated as a constant (e.g., as a known sensor parameter) or may be computed as a variable using multivariable estimation techniques. If offset is treated as a constant, then two parameters, $\chi$ and delay, may be estimated using calibration techniques. Otherwise, if offset is treated as a variable, then three parameters, offset, $\chi$ and delay, may be estimated. First, expression (15) may be transformed to a discrete format expression (18) in which:

$$BG \Delta t = \chi \times sumP \quad (18)$$

where:

$$sumP = \text{delay}(ISIG_1 - ISIG_0) + \frac{(ISIG_1 - \text{offset}) + (ISIG_0 - \text{offset})}{2} \Delta t;$$

BG is a blood glucose reference sample value obtained at a time $T_{BG}$;

$ISIG_0$ is a sample value of ISIG(t) obtained at a time $T_0$ preceding $T_{BG}$;

$ISIG_1$ is a sensor signal sample value of ISIG(t) obtained at a time $T_1$ following $T_{BG}$; and $\Delta t$ is a sampling interval between consecutive discrete samples of ISIG(t) to obtain $ISIG_0$ and $ISIG_1$ (e.g., $T_1 - T_0$).

In a particular implementation, values for $\chi$, delay and offset for use in computing SG(t) may be determined using any one of several least squares or "best fit" parameter estimation techniques by, for example, comparing a value of SG(t) computed according to expression (17) with a contemporaneous blood glucose reference sample BG. In one particular implementation, an initial value for $\chi$ may be computed according to expression (19) as follows:

$$\chi = \frac{\sum_i w_i^1 w_i^2 \text{sum} P_i BG_i}{\sum_i w_i^1 w_i^2 \text{sum} P_i^2} \quad (19)$$

where:

$w_i^1$ and $w_i^2$ are weight coefficients;

$BG_i$ is an ith blood glucose reference sample value; and $sumP_i$ is a value of sumP computed with blood glucose reference sample $BG_i$ and temporally correlated values for ISIG(t) (e.g., $ISIG_{0i}$ and $ISIG_{1i}$).

Coefficients $w_i^1$ and $w_i^2$ may be determined according to any one of several weighting functions. One such weighting function may more heavily weight more recent values of $sumP_i$ to account, for example, in changes in sensor performance over time (e.g., sensor drift). Another such weighting function may apply a weight according to an inverse variance function based on corresponding values for ISIG as discussed in U.S. patent application Ser. No. 12/345,477, filed on Dec. 29, 2008, incorporated herein by reference, and assigned to the assignee of claimed subject matter.

In one implementation, computation of an estimate for $\chi$ according to expression (19) may commence on having a minimum blood glucose reference measurements (e.g., two blood glucose reference measurements $BG_i$ stored in a buffer of controller 12). An initial value for delay may be selected (e.g., two to twenty minutes). A value for $\chi$ may be computed according to expression (19).

Values for $\chi$ and delay may be computed on a set cycle (e.g., twice per day). Upon computation of updated values for $\chi$ and delay, determination of $\Delta ISIG(t)$ in expression (17) may be determined as a difference between a new initial sensor signal value ISIG(t) and $ISIG(t_0)$.

A rate of change or derivative of a signal or function may be as set forth in expression (17), for example, may be computed using any one of several techniques described above, and claimed subject matter is not limited to any particular technique.

Figure 8:
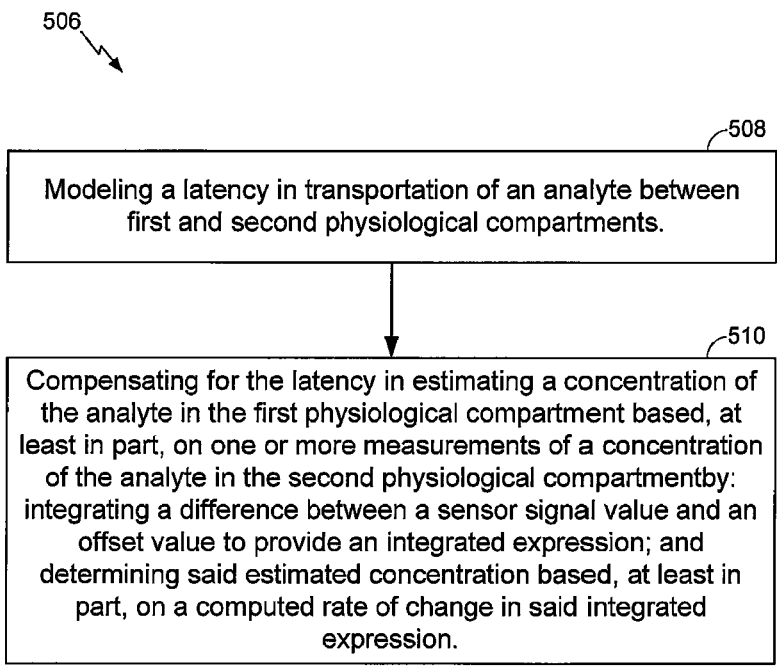
FIG. 8 is a flow diagram of a process for compensating for a latency in estimating a concentration of an analyte in physiological compartment according to an alternative embodiment.

FIG. 8 is a flow diagram of a process 506 to compensate for a delay or latency in transportation of an analyte between physiological compartments according to an alternative implementation (e.g., according to expressions (13) through (19) discussed above). A latency in the transportation an analyte between physiological compartments (ISF and blood plasma in particular examples below) is modeled at block 508. A process of estimating a concentration of the analyte present in one of the physiological compartments based upon an observed concentration of the analyte in the other physiological compartment may then compensate for this modeled latency at block 510. At block 510, however, a difference between a sensor signal value and an offset value is integrated to provide an integrated expression. The estimated concentration may then be based, at least in part, on a computed rate of change in the integrated expression.

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above systems, methods, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method at least partially executed by a computing apparatus comprising:
    modeling a latency in transportation of an analyte between first and second physiological compartments; and
    compensating for the latency in estimating a concentration of the analyte in the first physiological compartment based, at least in part, on one or more measurements of a concentration of the analyte in the second physiological compartment by:
        combining over time a difference between a sensor signal value and an offset value to provide an integration result;
        combining said integration result with a term based, at least in part, on said modeled latency to provide a combined expression; and
        determining said estimated concentration based, at least in part, on a computed rate of change in said combined expression.

2. The method of claim 1, wherein the analyte comprises glucose, the first physiological compartment comprises blood plasma, and the second physiological compartment comprises interstitial fluid.

3. The method of claim 1, wherein said sensor signal value comprises a measured current responsive to the concentration of said analyte in said second physiological compartment.

4. The method of claim 1, wherein the latency is based, at least in part, on a latency of a presence of glucose in a patient's interstitial fluid to affect a blood glucose concentration in said patient.

5. The method of claim 4, wherein the latency is defined based, at least in part, on a time for 63% of glucose in said interstitial fluid to be absorbed by the patient's blood.

6. An apparatus comprising:
    a sensor to generate a signal responsive to a concentration of an analyte in a second physiological compartment; and
    a processor configured to:
        model a latency in transportation of the analyte between the second physiological compartment and a first physiological compartment; and
        compensate for the latency in estimating a concentration of the analyte in the first physiological compartment based, at least in part, on the signal responsive to the concentration of the analyte in the second physiological compartment by:
        combining over time a difference between a sensor signal value and an offset value to provide an integration result;
        combining said integration result with a term based, at least in part, on said modeled latency to provide a combined expression; and
        determining said estimated concentration based, at least in part, on a computed rate of change in said combined expression.

7. The apparatus of claim 6, wherein said sensor signal value comprises a measured current responsive to the concentration of said analyte in said second physiological compartment.

8. The apparatus of claim 6, wherein the analyte comprises glucose, the first physiological compartment comprises blood plasma, and the second physiological compartment comprises interstitial fluid.

9. The apparatus of claim 6, wherein the latency is based, at least in part, on a latency of a presence of glucose in a patient's interstitial fluid to affect a blood glucose concentration in said patient.

10. The apparatus of claim 9, wherein the latency is defined based, at least in part, on a time for 63% of glucose in said interstitial fluid to be absorbed by the patient's blood.

11. The apparatus of claim 6, the processor configured further to generate a command to one or more infusion pumps computed based, at least in part, on said estimated concentration.

12. An article comprising:
a non-transitory storage medium having machine-readable instructions stored thereon which are executable by a special purpose computing apparatus to:
model a latency in transportation of an analyte between first and second physiological compartments; and
compensate for the latency in estimating a concentration of the analyte in the first physiological compartment based, at least in part, on one or more measurements of a concentration of the analyte in the second physiological compartment by:
combining over time a difference between a sensor signal value and an offset value to provide an integration result;
combining said integration result with a term based, at least in part, on said modeled latency to provide a combined expression; and
determining said estimated concentration based, at least in part, on a computed rate of change in said combined expression.

13. The article of claim 12, wherein the analyte comprises glucose, the first physiological compartment comprises blood plasma, and the second physiological compartment comprises interstitial fluid.

14. The article of claim 12, wherein said sensor signal value comprises a measured current responsive to the concentration of said analyte in said second physiological compartment.

15. An apparatus comprising:
means for modeling a latency in transportation of an analyte between first and second physiological compartments; and
means for compensating for the latency in estimating a concentration of the analyte in the first physiological compartment based, at least in part, on one or more measurements of a concentration of the analyte in the second physiological compartment by:
combining over time a difference between a sensor signal value and an offset value to provide an integration result;
combining said integration result with a term based, at least in part, on said modeled latency to provide a combined expression; and
determining said estimated concentration based, at least in part, on a computed rate of change in said combined expression.

* * * * *